United States Patent [19]

Franke

[11] 4,117,335
[45] Sep. 26, 1978

[54] X-RAY DIAGNOSTIC GENERATOR FOR THE PURPOSE OF FLUOROSCOPY AND PHOTOGRAPHY

[75] Inventor: Kurt Franke, Erlangen, Germany

[73] Assignee: Siemens Aktiengesellschaft, Berlin & Munich, Germany

[21] Appl. No.: 823,714

[22] Filed: Aug. 11, 1977

[30] Foreign Application Priority Data

Jan. 14, 1977 [DE] Fed. Rep. of Germany ....... 2701433

[51] Int. Cl.² ........................................... G03B 41/16
[52] U.S. Cl. ................................... 250/402; 250/409
[58] Field of Search ............... 250/401, 402, 408, 409, 250/413

[56] References Cited

U.S. PATENT DOCUMENTS

| | | | |
|---|---|---|---|
| 3,902,069 | 8/1975 | Sharke | 250/402 |
| 3,991,314 | 11/1976 | Schmitman | 250/402 |

*Primary Examiner*—Craig E. Church
*Attorney, Agent, or Firm*—Hill, Gross, Simpson, Van Santen, Steadman, Chiara & Simpson

[57] ABSTRACT

In a fluoroscopic and photographic exposure installation where photographic exposure high voltage is normally automatically derived from the voltage setting during fluoroscopy, a pair of manually operable switches are provided in the motor control circuit for inserting respective preselected reference levels which override the normal adjustment of exposure voltage based on fluoroscopic voltage, and instead control the exposure voltage selectively to a higher setting giving a particularly brief exposure, or to a relatively low value giving improved contrast.

1 Claim, 1 Drawing Figure

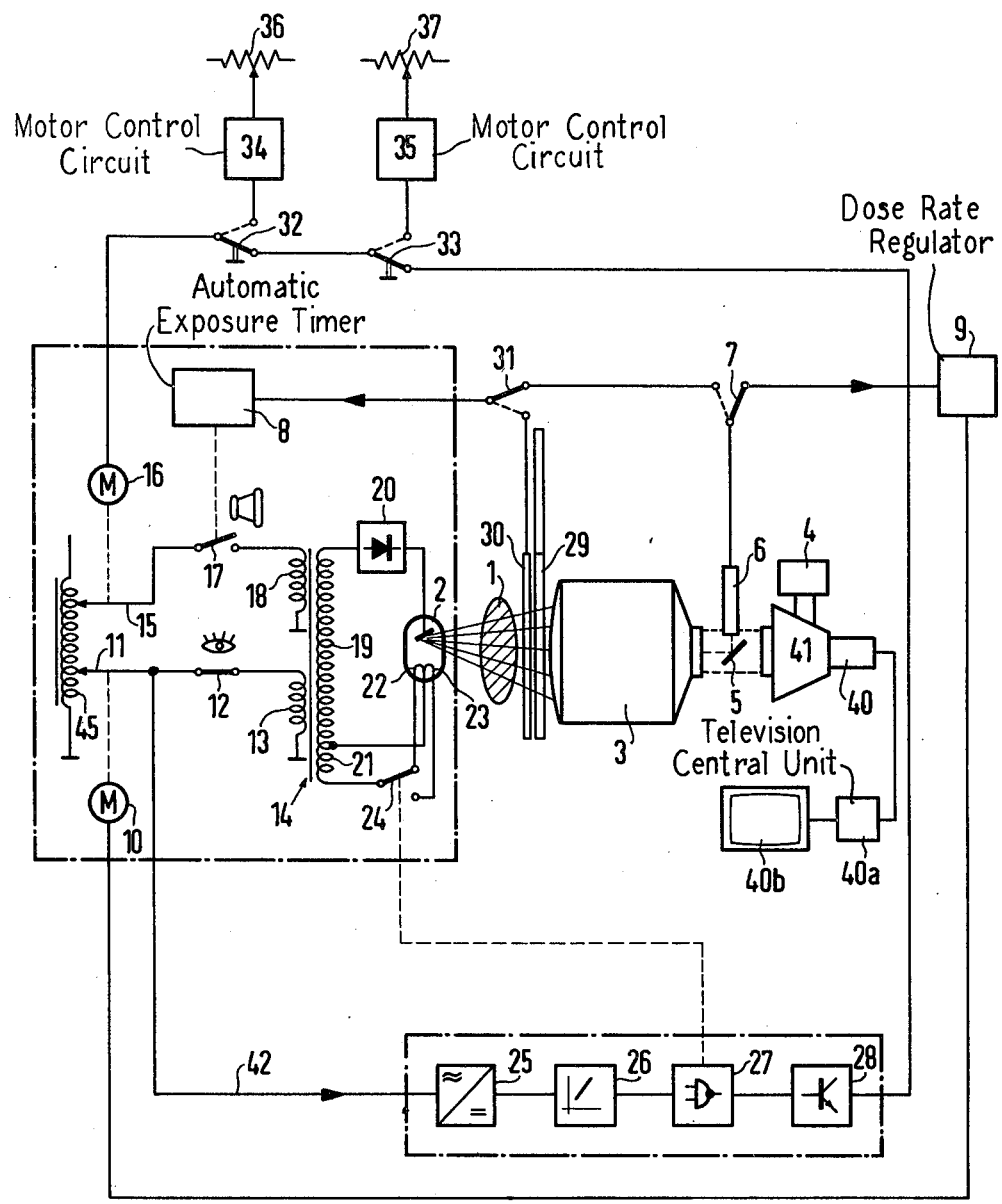

X-RAY DIAGNOSTIC GENERATOR FOR THE PURPOSE OF FLUOROSCOPY AND PHOTOGRAPHY

BACKGROUND OF THE INVENTION

The invention relates to an x-ray diagnostic generator for the purpose of fluoroscopy and photography comprising an image intensifier, an installation for regulating the dose rate during fluoroscopy, an automatic exposure timer and a function generator to which a signal is supplied corresponding to the respective fluoroscopy-x-ray tube voltage, said function generator forming from said signal an output signal controlling the adjustment means for the photographic exposure-x-ray tube voltage, and wherein the characteristic of the photographic exposure voltage is programmed as a function of the fluoroscopy voltage.

An x-ray diagnostic generator of this type is described in the U.S. Pat. No. 3,991,314. In the case of this x-ray diagnostic generator, the change in the x-ray tube voltage and in the x-ray tube current proceeds by means of the fluoroscopy regulating installation in accordance with a predetermined function for effecting the change in the dose rate. From the respective fluoroscopy-x-ray tube voltage, the photographic exposure-x-ray tube voltage automatically results during the transition to a photographic mode; i.e., this voltage need not be individually adjusted by hand. The known x-ray diagnostic generator is thus very simple in its operation.

It has been observed that in practice the automatically adjusted photographic exposure-x-ray tube voltage is not always optimal. For instance, it is sometimes desirable to produce particularly high-contrast-x-ray photographs with a low x-ray tube voltage, or to produce photographs of short duration with a high x-ray tube voltage.

SUMMARY OF THE INVENTION

The object which is the basis of the invention resides in producing an x-ray diagnostic generator of the type initially cited which allows for a manual selection of an x-ray tube voltage for high contrast photographs and an x-ray tube voltage for photographs of particularly short duration.

In accordance with the invention, this object is achieved by virtue of the fact that hand switches are provided by means of which the adjustment means for the photographic exposure-x-ray tube voltage can be selectively connected to a nominal value generator for producing a fixedly predetermined photographic exposure-x-ray tube voltage which is high in comparison with the photographic exposure x-ray tube voltage which is automatically adjusted for a patient of average constitution or which adjustment means can be selectively connected to a nominal value generator for a photographic exposure-x-ray tube voltage which is low in comparison with the x-ray tube voltage which is automatically adjusted for a patient of average constitution.

Other objects, features and advantages of the invention will be apparent from the following detailed description taken in connection with the accompanying sheet of drawings.

BRIEF DESCRIPTION OF THE DRAWINGS

The single FIGURE of drawings shows an illustrative embodiment of the invention by means of a schematic electric circuit diagram.

DETAILED DESCRIPTION

A patient, schematically illustrated in cross-section at 1, is irradiated by an x-ray tube 2. The images produced by the x-ray tube 2 are conveyed from an image intensifier 3 to a film camera 4 for the preparation of series photographs via an optical divider 41. Disposed between the output fluoroscent screen of the image intensifier 3 and the optical divider 41 there is disposed a mirror 5 which supplies a portion of the intensifier output to a photomultiplier 6. The photomultiplier 6 supplies at its output a signal corresponding to the brightness on the output fluorescent screen of image intensifier 3. Via a switch 7, photomultiplier 6 is capable of being selectively connected to an automatic exposure timer 8 or to a dose rate regulating device 9.

The output signal of the dose rate regulating device 9 controls a servo motor 10 for a tap 11 of a regulating transformer 45. Tap 11 determines the fluoroscopy-x-ray tube voltage which is supplied to a primary winding 13 of a high voltage transformer 14 via a switch 12 which is closed during fluoroscopy. The adjustment of the photographic exposure voltage proceeds by means of a tap 15 which is adjustable by a servo motor 16. The photographic exposure voltage is supplied to a primary winding 18 of the high voltage transformer 14 by a switch 17 which is closed during a photographic exposure. Switch 12 is then open. The circuit for energizing x-ray tube 2 supplies a high voltage thereto from a secondary winding 19 via a high-voltage rectifier 20. A secondary winding 21 of high-voltage transformer 14 selectively feeds two filament windings 22 and 23 of x-ray tube 2 which are associated with two different focuses. The selection of the respective desired filament winding 22 or 23 proceeds by means of a switch 24.

A signal corresponding to the actual fluoroscopy-x-ray tube voltage is conveyed to a voltage converter 25 via a line 42. Voltage converter 25 controls a function generator 26 which produces an output signal which, corresponding to a predetermined program stored in function generator 26, is dependent upon the input signal; i.e., upon the actual fluoroscopy x-ray tube voltage, and which as explained in U.S. Pat. No. 3,991,314 corresponds to a desired photographic exposure x-ray tube voltage associated with the fluoroscopy-x-ray tube voltage. The output signal of function generator 26 controls a switching stage 28 via logic 27. Switching stage 28 switches the regulating motor 16 on or off for the purpose of adjusting the respective photographic exposure-x-ray tube voltage. Switching stage 28 may e.g. be a component part of a follow-up control device. Logic 27 effects the switching over of switch 24; i.e., the selection of the respectively desired focus of the x-ray tube 2 as a funciton of the respectively automatically adjusted flurorscopy x-ray tube voltage.

During fluoroscopy, switches 7 and 12 occupy their fully illustrated (solid line) positions. Through the fluoroscopy regulating device 9 there takes place an adjustment of tap 11 and thus of the x-ray tube voltage and of the x-ray tube current such that brightness at the output fluorescent screen of the image intensifier 3 is kept constant. If a changeover is to be made from fluoroscopy to photography switch 12 is opened and switch 17 closed.

The photographic exposure voltage has already been adjusted during fluoroscopy in accordance with the respective desired program by means of motor 16, so that, upon closing switch 17, the correct voltage for the preparation of a series of photographs with camera 4 is already connected to the x-ray tube 2. Through logic 27, in addition, the correct focus of x-ray 2 has been selected; i.e., the correct filament winding 22 or 23 has been connected to the secondary winding 21. Accordingly, in the case of the illustrated x-ray diagnostic generator, it is possible to directly switch over from fluoroscopy to photography without the necessity of making a special adjustment of the photographic exposure x-ray tube voltage.

During a photographic exposure, switch 7 is also switched over into its position illustrated in broken lines, in which the automatic exposure timer 8 receives a signal corresponding to the dose rate behind the patient 1 which is supplied by photomultiplier 6 during operation with camera 4. The automatic exposure timer 8 effects the opening of switch 17 and thus the termination of a photographic exposure when the dose necessary for an optimal image density has been obtained.

In order to prepare direct photographs, an x-ray target device 29 is provided which allows for the insertion of a cassette with an x-ray film into the path of rays issuing directly from patient 1. Associated with x-ray target device 29 is a measuring chamber 30 which is capable of being connected (instead of photomultiplier 6) to the automatic exposure timer 8 via a switch 31. Thus, if direct photographs are made, switch 31 is changed over into its position illustrated by broken lines so that a signal is connected to its input which is supplied from said measuring chamber 30 and which corresponds to the respective dose rate on the film in the target device 29. This signal is integrated in the automatic exposure timer 8 and, when a predetermined dose has been reached, switch 17 is opened for the purpose of terminating the photographic exposure.

The control signal for the servo motor 16 proceeds via two switches 32 and 33, one of which, respectively, can be selectively manually switched into the position illustrated in broken lines. Associated with the hand switches 32 and 33 are control mechanisms 34 and 35, to which nominal value selectors 36 and 37 are connected. A photographic exposure x-ray tube voltage is adjusted at nominal value selector 36 which is high in comparison with the photographic exposure x-ray tube voltage automatically adjusted for a patient of average constitution, whereas a photographic x-ray tube voltage is adjusted at nominal value selector 37 which is low in comparison with the photographic exposure x-ray tube voltage automatically adjusted for a patient of average constitution. Accordingly, if e.g. by means of target device 29, a particularly high-contrast photograph is to be made, switch 33 is manually changed over into its position illustrated in broken lines, so that motor 16 adjusts tap 15 to supply a photographic x-ray tube voltage resulting in good contrast. Conversely, for the preparation of an x-ray photograph of particularly short duration; e.g. by means of target device 29, which x-ray photograph manifests very little motional blurring, switch 32 is changed over into its position illustrated in broken lines so that motor 16 adjusts tap 15 to supply the x-ray tube high voltage predetermined by nominal value selector 36.

Control devices 34 and 35 may be follow-up motor control circuits. For example, where as shown in the fifth figure of U.S. Pat. No. 3,991,314, the exposure voltage adjusting motor is mechanically coupled to a movable contact (76) of a feedback potentiometer (75), the circuits 34 and 35 may include similar feedback potentiometers whose movable contacts are also driven by the output of motor 16. Circuits 34 and 35 would also include comparators corresponding to comparison member (74) of the fifth figure of U.S. Pat. No. 3,991,314, each receiving inputs from the respective reference value selector 36 or 37 and from the respective feedback potentiometer. Thus the output of the respective comparators of components 34 and 35 override the normal adjustment control means 28 when switch 32 or 33 is manually actuated, and adjustment motor 16 is controlled according to the predetermined setting of reference value selector 36 or 37, respectively.

In the sample embodiment, the x-ray image is picked up by a television camera tube 40 at the output of the image intensifier 3 during fluoroscopy, and is reproduced via a television cental unit 40a on a video display unit 40b.

It will be apparent that many modifications and variations may be effected without departing from the scope of the novel concepts and teachings of the present invention.

I claim as my invention:

1. X-ray diagnostic generator for the purpose of fluoroscopy and photography comprising an image intensifier, an installation for regulating the dose rate during fluoroscopy, adjustment means for determining the photographic exposure x-ray tube voltage, an automatic exposure timer and a function generator to which a signal is supplied corresponding to the respective fluoroscopy x-ray tube voltage, which forms from the signal an output signal for controlling the adjustment means for the photographic exposure-x-ray tube voltage, and in which the characteristic of the photographic exposure voltage is programmed as a function of the fluoroscopy voltage, characterized in that hand switches (32, 33) are provided by means of which the adjustment means (16) for the photographic exposure-x-ray tube voltage can be selectively connected to a nominal value selector (36) for a fixedly predetermined photographic exposure-x-ray tube voltage which is high in comparison with the photographic exposure-x-ray tube voltage automatically adjusted for a patient of average constitution, or which can be connected to a nominal value selector (37) for a photographic exposure-x-ray tube voltage which is low in comparison with the x-ray tube voltage automatically adjusted for a patient of average constitution.

* * * * *